(12) United States Patent
Bishop-Hurley et al.

(10) Patent No.: US 7,238,669 B2
(45) Date of Patent: Jul. 3, 2007

(54) PHAGE-DISPLAY PEPTIDES AS NOVEL ANTIMICROBIAL AGENTS AGAINST HAEMOPHILUS INFLUENZAE

(75) Inventors: Sharon L. Bishop-Hurley, Yeppoon (AU); Francis J. Schmidt, Columbia, MO (US); Arnold L. Smith, Mercer Island, WA (US)

(73) Assignee: The Curators of the University of Missouri, Columbia, MO (US)

( * ) Notice: Subject to any disclaimer, the term of this patent is extended or adjusted under 35 U.S.C. 154(b) by 194 days.

(21) Appl. No.: 10/655,562

(22) Filed: Sep. 4, 2003

(65) Prior Publication Data

US 2005/0037972 A1    Feb. 17, 2005

Related U.S. Application Data

(60) Provisional application No. 60/409,909, filed on Sep. 11, 2002.

(51) Int. Cl.
| | |
|---|---|
| A61K 38/10 | (2006.01) |
| A61L 27/34 | (2006.01) |
| A61L 101/46 | (2006.01) |
| C07K 7/08 | (2006.01) |
| G01N 33/53 | (2006.01) |

(52) U.S. Cl. ............ 514/14; 422/28; 427/2.1; 427/2.24; 427/2.3; 436/501; 530/326
(58) Field of Classification Search .............. None
See application file for complete search history.

(56) References Cited

U.S. PATENT DOCUMENTS

| | | | | |
|---|---|---|---|---|
| 5,466,671 | A | * 11/1995 | Tempst et al. ............... 514/13 |
| 6,020,154 | A | 2/2000 | Hansen et al. ............ 435/69.1 |
| 6,180,604 | B1 | * 1/2001 | Fraser et al. ............... 514/12 |
| 2003/0143671 | A1 | * 7/2003 | Adler et al. ............... 435/69.1 |

OTHER PUBLICATIONS

Boyle-Vavra et al., "Reversion of the glycopeptide resistance phenotype in Staphylococcus aureus clinical isolates," Antimicrob. Agents Chemother., 44(2):272-277, 2000.

* cited by examiner

Primary Examiner—Jeffrey Edwin Russel
(74) Attorney, Agent, or Firm—Fulbright & Jaworski, LLP

(57) ABSTRACT

Whole cell phage-display techniques were used to identify several peptides that bound preferentially to a non-typeable strain of Haemophilus influenzae. These peptides were able to inhibit growth of both H. influenzae and Staphylococcal aureus. Thus, methods for treating bacterial infections, alone or in combination with traditional antibiotics, are envisioned.

40 Claims, 6 Drawing Sheets

PHAGE-DISPLAY PEPTIDES AS NOVEL ANTIMICROBIAL AGENTS AGAINST HAEMOPHILUS INFLUENZAE

This application claims benefit of priority to U.S. Provisional Ser. No. 60/409,909, filed Sep. 11, 2002, the entire contents of which are hereby incorporated by reference.

The government owns rights in the present invention pursuant to grant number DHHS 5 RO1 AI44002-02 from the National Institutes of Health.

BACKGROUND OF THE INVENTION

A. Field of the Invention

The present invention relates to the fields of microbiology and infectious pathology. More particularly, it deals with the identification of peptides that are capable of inhibiting bacterial infections, including those caused by *Haemophilus influenzae* and *Staphylococcus aureus*.

B. Related Art

Nasopharyngeal colonization with non-encapsulated *Haemophilus influenzae* (NTHi) frequently occurs in infants and in adults with common variable immunodeficiency (CVID), but is rarely found among healthy adults. In children with recurrent episodes of acute otitis media (RAOM), NTHi is more common than in healthy individuals. Protracted nasopharyngeal colonization with one and the same NTHi strain has also been found in CVID patients. Colonization is suspected to cause deeper infections, e.g., sinusitis and pneumonia. Since they early 1990's, however, there has been an increase in invasive NTHi infections in previously healthy people.

Similarly, *Staphylococcus aureus* clinical isolates with intermediate resistance to glycopeptides, so called GISA isolates, have recently been recognized in Japan, the U.S. and elsewhere (Ploy et al., 1998; Wong et al., 1999). GISA isolates described to date have been uniformly resistant to methicillin and have sorted into three phenotypic classes (Boyle-Vavra et al., 2000). All are heteroresistant in that only a subpopulation of cells express the vancomycin resistance phenotype. Class A isolates are intermediate to vancomycin and teicoplanin; class B isolates are intermediate to vancomycin but susceptible to teicoplanin. Class C isolates have an MIC of teicoplanin in the intermediate range and vancomycin in the susceptible range (Boyle-Vavra et al., 2000). Additionally, isolates have been described that are susceptible to both glycopeptides by minimum inhibitory concentration (MIC) testing, but contain a subpopulation that can survive on vancomycin >4 µg/ml. The mechanism of glycopeptide resistance in *S. aureus* remains unclear.

Thus, there is a growing need to identify new and improved antibiotics that are effective at preventing and treating these difficult to treat and quite dangerous bacterial infections.

SUMMARY OF THE INVENTION

Thus, in accordance with the present invention, there is provided a method for inhibiting the growth of a *Staphylococcal* or *Haemophilus* species comprising contacting the species with a peptide comprising the sequence KQRDSRSGYTAPTLV (SEQ ID NO:1), KKSHHPSSEWGLNLT (SEQ ID NO:2), GRHRTSVPTDEVFIT (SEQ ID NO:3), KQRTSIRATEGCLPS (SEQ ID NO:4), RNHGTDRATTIPPLS (SEQ ID NO:5), GSRGKHTFVRPTLVF (SEQ ID NO:6), FISYSSPSHMGARMR (SEQ ID NO:7) and/or VVFLSSRNSAVFTDF (SEQ ID NO:8). The species is a *Staphyloccocal* species, for example, *S. aureus*. The species may also be a *Haemophilus* species, such as *H. influenzae*, including non-typeable *H. influenzae*. The peptide may be between 15 and about 50 residues in length, between about 15 and 25 residues in length, or 15 residues in length. The method may further comprise contacting the species with a chemopharmaceutical antibiotic.

In another embodiment, there is provided a method for treating a bacterial infection in a subject comprising contacting the subject with a peptide comprising the sequence KQRDSRSGYTAPTLV (SEQ ID NO:1), KKSHHPSSEWGLNLT (SEQ ID NO:2), GRHRTSVPTDEVFIT (SEQ ID NO:3), KQRTSIRATEGCLPS (SEQ ID NO:4), RNHGTDRATTIPPLS (SEQ ID NO:5), GSRGKHTFVRPTLVF (SEQ ID NO:6), FISYSSPSHMGARMR (SEQ ID NO:7) and/or VVFLSSRNSAVFTDF (SEQ ID NO:8) in an amount sufficient to inhibit the growth of bacteria in vivo. The species is a *Staphyloccocal* species, for example, *S. aureus*. The species may also be a *Haemophilus* species, such as *H. influenzae*, including non-typeable *H. influenzae*. The peptide may be between 15 and about 50 residues in length, between about 15 and 25 residues in length, or 15 residues in length. The method may further comprise contacting the species with a chemopharmaceutical antibiotic. The peptide may be delivered local or regional to a site of infection, or to a wound site. The peptide may be administered topically, systemically, or via intravenous or intraarterial injection. The method may further comprise administering to the subject a chemopharmaceutical antibiotic.

In yet another embodiment, there is provided a method for preventing a bacterial infection in a subject comprising contacting the subject with a peptide comprising the sequence KQRDSRSGYTAPTLV (SEQ ID NO:1), KKSHHPSSEWGLNLT (SEQ ID NO:2), GRHRTSVPTDEVFIT (SEQ ID NO:3), KQRTSIRATEGCLPS (SEQ ID NO:4), RNHGTDRATTIPPLS (SEQ ID NO:5), GSRGKHTFVRPTLVF (SEQ ID NO:6), FISYSSPSHMGARMR (SEQ ID NO:7) and/or VVFLSSRNSAVFTDF (SEQ ID NO:8) in an amount sufficient to inhibit the growth of bacteria in vivo.

In still yet another embodiment, there is provided a method for preventing bacterial growth in a solution comprising mixing the solution with a peptide comprising the sequence KQRDSRSGYTAPTLV (SEQ ID NO:1), KKSHHPSSEWGLNLT (SEQ ID NO:2), GRHRTSVPTDEVFIT (SEQ ID NO:3), KQRTSIRATEGCLPS (SEQ ID NO:4), RNHGTDRATTIPPLS (SEQ ID NO:5), GSRGKHTFVRPTLVF (SEQ ID NO:6), FISYSSPSHMGARMR (SEQ ID NO:7) and/or VVFLSSRNSAVFTDF (SEQ ID NO:8) in an amount sufficient to inhibit the growth of bacteria in vivo.

In an additional embodiment, there is provided a method for preventing bacterial attachment or growth on an abiotic surface comprising coating the surface with a peptide comprising the sequence KQRDSRSGYTAPTLV (SEQ ID NO:1), KKSHHPSSEWGLNLT (SEQ ID NO:2), GRHRTSVPTDEVFIT (SEQ ID NO:3), KQRTSIRATEGCLPS (SEQ ID NO:4), RNHGTDRATTIPPLS (SEQ ID NO:5), GSRGKHTFVRPTLVF (SEQ ID NO:6), FISYSSPSHMGARMR (SEQ ID NO:7) and/or VVFLSSRNSAVFTDF (SEQ ID NO:8) in an amount sufficient to inhibit the growth of bacteria in vivo. The surface may be part of a medical device, such as in a syringe, a stent, a catheter, fluid container, a pacemaker, or an implantable pump.

In yet additional embodiments, there is provided a medical device, a surface of which is coated with a peptide comprising the sequence KQRDSRSGYTAPTLV (SEQ ID NO:1), KKSHHPSSEWGLNLT (SEQ ID NO:2), GRHRTSVPTDEVFIT (SEQ ID NO:3), KQRTSIRATEGCLPS (SEQ ID NO:4), RNHGTDRATTIPPLS (SEQ ID NO:5), GSRGKHTFVRPTLVF (SEQ ID NO:6), FISYSSPSHMGARMR (SEQ ID NO:7) and/or VVFLSSRNSAVFTDF (SEQ ID NO:8) in an amount sufficient to inhibit the growth of bacteria in vivo. The medical device may be a syringe, a stent, a catheter, fluid container, a pacemaker, or an implantable pump. The medical device may be coated with a second antibiotic agent.

Another embodiment comprises a method of screening a phage display library against intact virulent *Haemophilus influenzae* comprising (a) providing a phage library; (b) providing intact virulent *H. influenzae*; (c) contacting the phage library with the *H. influenzae*; (d) obtaining phage bound to the *H. influenzae*; and (e) determining the sequence of a peptide expressed in the phage library that binds to the *H. influenzae*. The method may further comprise: performing subtractive affinity selection of bound phage against avirulent *H. influenzae*; assessing the effect of a peptide that binds the *H. influenzae* on bacterial surface adherence; assessing the effect of a peptide that binds the *H. influenzae* on bacterial growth; and/or assessing surface adherence or growth of a second bacterial species in the presence of the peptide. Steps (c) and (d) may be repeated at least once.

Yet another embodiment comprises a peptide identified according to a method comprising the steps of (a) providing a phage library; (b) providing intact virulent *H. influenzae*; (c) contacting the phage library with the *H. influenzae*; (d) obtaining phage bound to the *H. influenzae*; (e) performing subtractive affinity selection against avirulent *H. influenzae*; and (f) determining the sequence of a peptide expressed in the phage library that binds to the *H. influenzae*. The peptide may be an isolated peptide of 15 to about 50 residues comprising the sequence KQRDSRSGYTAPTLV (SEQ ID NO:1), KKSHHPSSEWGLNLT (SEQ ID NO:2), GRHRTSVPTDEVFIT (SEQ ID NO:3), KQRTSIRATEGCLPS (SEQ ID NO:4), RNHGTDRATTIPPLS (SEQ ID NO:5), VVFLSSRNSAVFTDF (SEQ ID NO:6), GSRGKHTFVRPTLVF (SEQ ID NO:7), or FISYSSPSHMGARMR (SEQ ID NO:8).

Also provided is a method for identifying a bacterial receptor comprising (a) providing a sample suspected of comprising a bacterial receptor; (b) providing a peptide comprising the sequence KQRDSRSGYTAPTLV (SEQ ID NO:1), KKSHHPSSEWGLNLT (SEQ ID NO:2), GRHRTSVPTDEVFIT (SEQ ID NO:3), KQRTSIRATEGCLPS (SEQ ID NO:4), RNHGTDRATTIPPLS (SEQ ID NO:5), VVFLSSRNSAVFTDF (SEQ ID NO:6), GSRGKHTFVRPTLVF (SEQ ID NO:7), or FISYSSPSHMGARMR (SEQ ID NO:8); (c) contacting the sample with the peptide; and (d) identifying a receptor that binds to the peptide. The sample may be a whole bacterium or a bacterial cell wall. The peptide may be fixed to a support, such as a filter, a column, a bead, a dipstick or a gel. The method may further comprise degradative sequencing of said identified receptor, may further comprise designing a degenerative probe based on the sequence of said identified receptor, may further comprise using the degenerative probe to identify the gene encoding the identified receptor.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

DETAILED DESCRIPTION OF THE INVENTION

Figure 1:
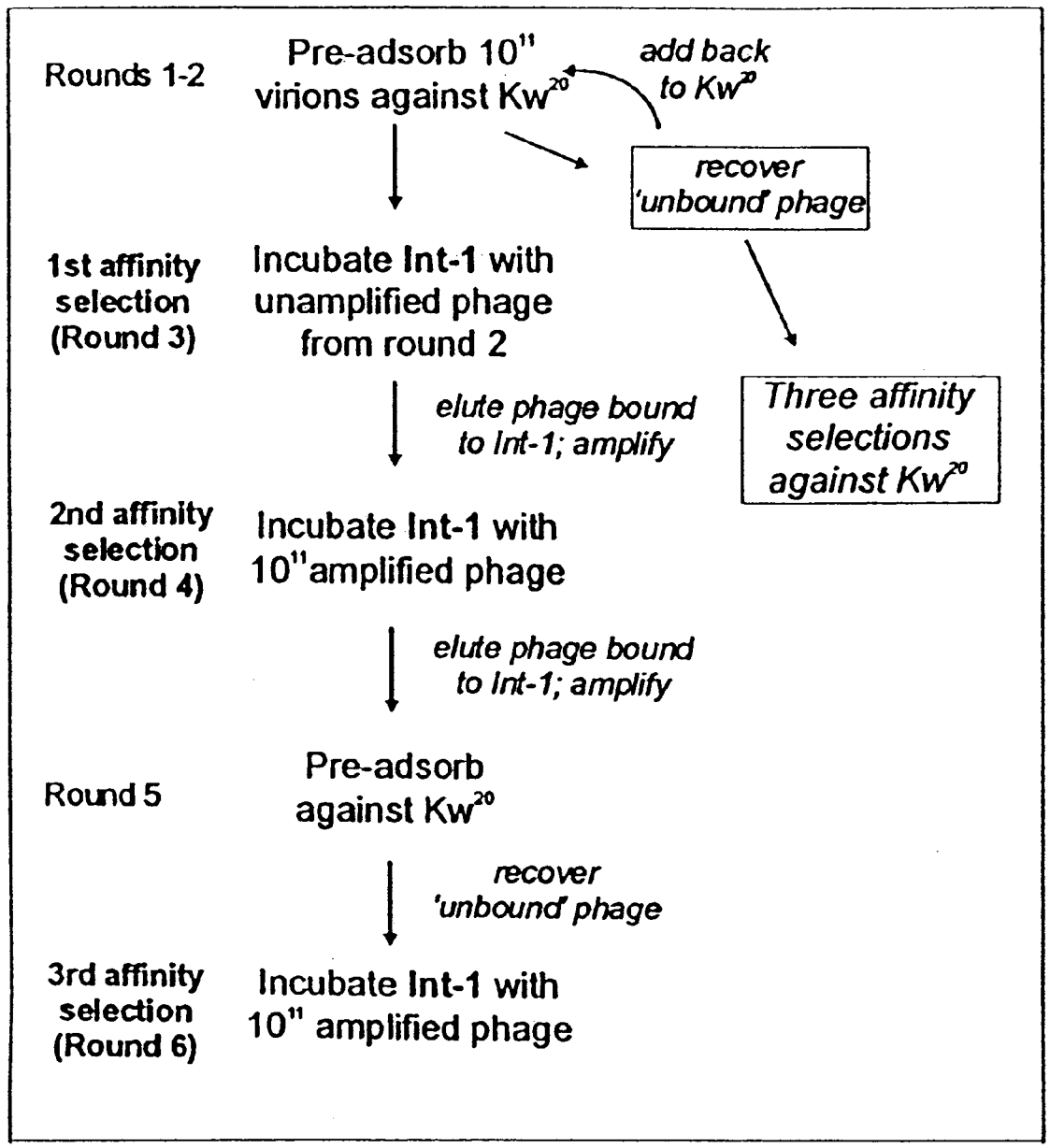
FIG. 1—Outline of the subtractive affinity selection procedure used to isolate phage peptides binding to the Int-1 strain of NTHi. Phage peptides were twice adsorbed to $Kw^{20}$ with no amplification in between. The peptides not binding to $Kw^{20}$ were affinity selected against Int-1 for a total of three affinity selection and two amplification steps. In addition, peptides binding to $Kw^{20}$ in the pre-adsorption steps were affinity selected three times against $Kw^{20}$.

As discussed above, there remains a need to find new anti-bacterial agents for use against microbial pathogens, in particular, for those organism that prove difficult to treat with conventional drugs.

The present inventors used a whole cell phage-display technique to isolate novel peptide epitopes that bind specifically to the cell surface of a NTHi strain of *H. influenzae*, designated Int-1. From the identified peptides, the inventors then isolated anti-microbial peptides that were bacteriostatic and/or bactericidal against *H. influenzae* strains. In addition, activity against *Staphylococcus aureus* was observed. These and other aspects of the invention are described in greater detail below.

A. Bacterial Infections

1. *Haemophilus Influenzae*

*Haemophilus influenzae* is a small, non-motile Gram-negative bacterium in the family Pasteurellaceae, on the level with the Vibrionaceae and the Enterobacteriaceae. The family also includes *Pasteurella* and *Actinobacillus*, two other genera of bacteria that are parasites of animals. Encapsulated strains of *Haemophilus influenzae* isolated from cerebrospinal fluid are coccobacilli, 0.2 to 0.3 to 0.5 to 0.8 µm, similar in morphology to *Bordetella pertussis*, the agent of whooping cough. Non-encapsulated organisms from sputum are pleomorphic and often exhibit long threads and filaments. The organism may appear Gram-positive unless the Gram stain procedure is very carefully carried out. Furthermore, elongated forms from sputum may exhibit bipolar staining, leading to an erroneous diagnosis of *Streptococcus pneumoniae*.

*Haemophilus influenzae* type b (Hib) used to be the most frequent cause of neonatal meningitis and other invasive infections of infants and young children in the United States (Fraser et al., 1974). Children of the susceptible age range, 6 months to 4 years, generally lack antibodies to the Hib capsular polysaccharide, which is a target for antibodies protective against systemic Hib disease. Moreover, children under the age of 2 years sometimes respond poorly to currently available polysaccharide-based vaccines such as pneumococcal vaccine or the Hib vaccine. For this reason, some vaccines containing only capsular polysaccharides are of limited utility in the case of young children, the group most at risk for severe Hib infections.

Though young children are sometimes poor responders to these vaccines, it has been reported that children in this age group respond to protein-based immunogens (Tiller and Buckley, 1978). An efficacious vaccine against Hib was developed by conjugating the capsular polysaccharide from Hib to a toxoid protein and is currently being sold under the trademark HibTITER™ (Lederle-Praxis Biologicals). However, this vaccine is not effective against disease caused by non-typeable *Haemophilus influenzae* (NTHi).

NTHi strains are known to be agents of diseases such as pneumonia, bacteremia, meningitis and postpartum sepsis (Murphy et al., 1985). In particular, NTHi is a frequent etiological agent of otitis media in children and young adults, causing 20–40% of all otitis media cases. Children may experience multiple infections due to the same organism as infection generally confers no long-lasting immunity. Current therapy for chronic or repeated occurrences of otitis media includes the administration of antibiotics and the insertion of tubes to drain the inner ear. Unfortunately, at the present time, no effective vaccine is available for the treatment of these infections.

In attempts to develop vaccines that are effective against NTHi, researchers have examined the immunogenicity of other, non-capsular Hib antigens. For example, it has been reported that passive immunization with antibodies directed against non-capsular Hib antigens served to protect against experimental Hib bacteremia (Shenep et al., 1983). A number of Hib protein components have been studied as possible candidates for the production of passive or active immunoreagents. Proteins that are present at the outer membrane are more likely to be exposed, or available for antibody binding, than are more internally localized proteins. Antibodies directed against Hib outer membrane proteins have been reported to confer protection against bacteremia following intraperitoneal challenge with Hib, whereas antibodies against lipopolysaccharide components lacked protective activity (Shenep et al., 1983). However, some Hib proteins have proven to be either insufficiently antigenic, or their corresponding antibody non-protective (Granoff et al., 1986).

Certain envelope components that could be investigated as potential vaccines include the components of the macromolecular structures that interact with heme and hence allow heme uptake by *H. influenzae*. Elements proposed to be involved in this system to date include a periplasmic lipoprotein that binds heme and has structural similarity to an *Escherichia coli* dipeptide permease (Hanson and Hansen, 1991; Hanson et al., 1992) and a 39 kDa heme-binding protein reported to be present on the *H. influenzae* cell surface (Lee, 1992). U.S. Pat. No. 6,020,154 to Hansen et al. disclosed hxuB and hxuC proteins from *H. influenzae* which, being surface expressed, were contemplated for use in the preparation of vaccines against pathological *H. influenzae* infections.

It is clear that while a variety of approaches to the treatment of bacterial diseases have experienced some success, the growing problems of antibiotic resistance, variability of antigens between species and in the same species through mutation of antigens, and the inefficient immune systems in young children and others, all present difficulties that need to be overcome. Thus, there exists today an immediate need for an effective treatment for NTHi *H. influenzae* pathogens that can be used for a variety of infections and in all patients.

2. *Staphylococcus Aureus*

*Staphylococcus aureus* is a ubiquitous pathogen and the etiological agent of a variety of conditions, ranging in severity from mild to fatal. *Staphylococcus aureus* causes a variety of suppurative infections and toxinoses in humans. It causes superficial lesions such as boils, styes and furuncles, more serious infections such as pneumonia, mastitis, phlebitis, meningitis, eyelid infections, neonatal conjunctivitis, skin and urinary tract infections, and deep-seated infections, such as joint infections, osteomyelitis and endocarditis. *S. aureus* is a major cause of nosocomial infections, particularly those involving surgical wounds, burns and infections associated with indwelling medical devices. *S. aureus* also causes food poisoning by releasing enterotoxins into food, and toxic shock syndrome by release of pyrogenic exotoxins into the blood stream.

*Staphylococci* are Gram-positive spherical bacteria that occur in microscopic clusters resembling grapes. Bacteriological culture of the nose and skin of normal humans invariably yields *staphylococci*. In 1884, Rosenbach described the two pigmented colony types of *staphylococci* and proposed the appropriate nomenclature: *Staphylococcus aureus* (yellow) and *Staphylococcus albus* (white). The latter species is now named *Staphylococcus epidermidis*. Although nineteen species of *Staphylococcus* are described in Bergey's Manual (1992), only *Staphylococcus aureus* and *Staphylococcus epidermidis* are significant in their interactions with humans. *S. aureus* colonizes mainly the nasal passages, but it may be found regularly in most other anatomical locales.

Taxonomically, the genus *Staphylococcus* is in the bacterial family Micrococcaceae, but the *staphylococci* are phylogenetically-unrelated to any other genera in the family. A wide variety of genetic criteria indicate that the genus *Staphylococcus* forms a coherent and well-defined natural group that is widely divergent from the genus *Micrococcus*. On the basis of 16S RNA analysis, the genus *Staphylococcus* belongs to the broad *Bacillus-Lactobacillus-Streptococcus* cluster. The closest relatives of *staphylococci* appear to be the *planococci, enterococci,* and *bacilli*. The closest relatives of *Micrococcus* are the arthrobacters.

*Staphylococcus aureus* forms a fairly large yellow colony on rich medium, and is often hemolytic on blood agar. *Staphylococci* are facultative anaerobes that grow by aerobic respiration or by fermentation that yields principally lactic acid. The bacteria are catalase-positive and oxidase-negative. *S. aureus* can grow at a temperature range of 15 to 45° C. and at NaCl concentrations as high as 15%. Nearly all strains of *S. aureus* produce the enzyme coagulase. In sum, *S. aureus* should always be considered a potential pathogen.

Staphylococci are perfectly spherical cells about 1 μm in diameter. They grow in clusters because *staphylococci* divide in two planes. The configuration of the cocci helps to distinguish *staphylococci* from *streptococci*, which are slightly oblong cells that usually grow in chains (because they divide in one plane only). The catalase test is important in distinguishing *streptococci* (catalase-negative) from *staphylococci*, which are vigorous catalase-producers. The test is performed by adding 3% hydrogen peroxide to a colony on an agar plate or slant. Catalase-positive cultures produce $O_2$ and bubble at once. The test should not be done on blood agar because blood itself contains catalase.

*Staphylococcus aureus* clinical isolates with intermediate resistance to glycopeptides, so called GISA isolates, have recently been recognized in Japan, the U.S. and elsewhere (Ploy et al., 1998; Wong et al, 1999). The low-level resistance of these isolates and the lack of hybridization with enterococcal glycopeptide resistance genes suggest that the glycopeptide resistance mechanisms in *staphylococci* are distinct from those mediating glycopeptide resistance in *Enterococcus* spp.

GISA isolates described to date have been uniformly resistant to methicillin and have sorted into three phenotypic classes (Boyle-Vavra et al., 2000). All are heteroresistant in that only a subpopulation of cells express the vancomycin resistance phenotype. Class A isolates are intermediate to vancomycin and teicoplanin; class B isolates are intermediate to vancomycin but susceptible to teicoplanin. Class C isolates have an MIC of teicoplanin in the intermediate range and vancomycin in the susceptible range (Boyle-Vavra et al., 2000). Additionally, isolates have been described that are susceptible to both glycopeptides by minimum inhibitory concentration (MIC) testing, but contain a subpopulation that can survive on vancomycin >4 μg/ml.

Typically, antibiotic resistance in *S. aureus* may be mediated by chromosomes or plasmids. *Staphylococci* exchange genetic material by various mechanisms, including transduction and cell-to-cell contact (Udo et al., 1992). Recent evidence is accumulating in favor of transfer of plasmids between *S. aureus* and *S. epidermidis*. Regardless of the mechanism of resistance, these new strains present a serious health threat to both industrialized and non-industrialized countries.

B. Peptides

The present invention focuses on eight peptides identified as binding preferentially to NTHi strains of *H. influenzae*. These peptides are KQRDSRSGYTAPTLV (SEQ ID NO:1), KKSHHPSSEWGLNLT (SEQ ID NO:2), GRHRTSVPTDEVFIT (SEQ ID NO:3), KQRTSIRATEGCLPS (SEQ ID NO:4), RNHGTDRATTIPPLS (SEQ ID NO:5), VVFLSSRNSAVFTDF (SEQ ID NO:6), GSRGKHTFVRPTLVF (SEQ ID NO:7), or FISYSSPSHMGARMR (SEQ ID NO:8).

It will be advantageous to produce peptides using the solid-phase synthetic techniques (Merrifield, 1963). Other peptide synthesis techniques are well known to those of skill in the art (Bodanszky et al., 1976; Peptide Synthesis, 1985; Solid Phase Peptide Synthelia, 1984). Appropriate protective groups for use in such syntheses will be found in the above texts, as well as in Protective Groups in Organic Chemistry, 1973. These synthetic methods involve the sequential addition of one or more amino acid residues or suitable protected amino acid residues to a growing peptide chain. Normally, either the amino or carboxyl group of the first amino acid residue is protected by a suitable, selectively removable protecting group. A different, selectively removable protecting group is utilized for amino acids containing a reactive side group, such as lysine.

Using solid phase synthesis as an example, the protected or derivatized amino acid is attached to an inert solid support through its unprotected carboxyl or amino group. The protecting group of the amino or carboxyl group is then selectively removed and the next amino acid in the sequence having the complementary (amino or carboxyl) group suitably protected is admixed and reacted with the residue already attached to the solid support. The protecting group of the amino or carboxyl group is then removed from this newly added amino acid residue, and the next amino acid (suitably protected) is then added, and so forth. After all the desired amino acids have been linked in the proper sequence, any remaining terminal and side group protecting groups (and solid support) are removed sequentially or concurrently, to provide the final peptide. The peptides of the invention are preferably devoid of benzylated or methylbenzylated amino acids. Such protecting group moieties may be used in the course of synthesis, but they are removed before the peptides are used. Additional reactions may be necessary, as described elsewhere, to form intramolecular linkages to restrain conformation.

In certain embodiments, it may prove useful to link other agents to the peptides of the present invention, for example, antibiotic agents. Bifunctional cross-linking reagents have been extensively used for a variety of purposes including preparation of affinity matrices, modification and stabilization of diverse structures, identification of ligand and receptor binding sites, and structural studies. Homobifunctional reagents that carry two identical functional groups proved to be highly efficient in inducing cross-linking between identical and different macromolecules or subunits of a macromolecule, and linking of polypeptide ligands to their specific binding sites. Heterobifunctional reagents contain two different functional groups. By taking advantage of the differential reactivities of the two different functional groups, cross-linking can be controlled both selectively and sequentially. The bifunctional cross-linking reagents can be divided according to the specificity of their functional groups, e.g., amino, sulfhydryl, guanidino, indole, carboxyl specific groups. Of these, reagents directed to free amino groups have become especially popular because of their commercial availability, ease of synthesis and the mild reaction conditions under which they can be applied. A majority of heterobifunctional cross-linking reagents contains a primary amine-reactive group and a thiol-reactive group.

Exemplary methods for cross-linking ligands to liposomes are described in U.S. Pat. No. 5,603,872 and U.S. Pat. No. 5,401,511, each specifically incorporated herein by reference in its entirety). Various agents can be covalently bound to peptides through the cross-linking of amine residues. Liposomes, in particular, multilamellar vesicles electrophilic maleimide residue, allowing coupling in one example, of aldehydes to free thiols. The cross-linking reagent can be modified to cross-link various functional groups and is thus useful for cross-linking polypeptides. Table 1 details certain hetero-bifunctional cross-linkers considered useful in the present invention.

TABLE 1

HETERO-BIFUNCTIONAL CROSS-LINKERS

| Linker | Reactive Toward | Advantages and Applications | Spacer Arm Length/ after cross-linking |
| --- | --- | --- | --- |
| SMPT | Primary amines Sulfhydryls | Greater stability | 11.2 A |
| SPDP | Primary amines Sulfhydryls | Thiolation Cleavable cross-linking | 6.8 A |
| LC-SPDP | Primary amines Sulfhydryls | Extended spacer arm | 15.6 A |
| Sulfo-LC-SPDP | Primary amines Sulfhydryls | Extended spacer arm Water-soluble | 15.6 A |
| SMCC | Primary amines Sulfhydryls | Stable maleimide reactive group Enzyme-antibody conjugation Hapten-carrier protein conjugation | 11.6 A |
| Sulfo-SMCC | Primary amines Sulfhydryls | Stable maleimide reactive group Water-soluble Enzyme-antibody conjugation | 11.6 A |
| MBS | Primary amines Sulfhydryls | Enzyme-antibody conjugation Hapten-carrier protein conjugation | 9.9 A |
| Sulfo-MBS | Primary amines Sulfhydryls | Water-soluble | 9.9 A |
| SIAB | Primary amines Sulfhydryls | Enzyme-antibody conjugation | 10.6 A |
| Sulfo-SIAB | Primary amines Sulfhydryls | Water-soluble | 10.6 A |
| SMPB | Primary amines Sulfhydryls | Extended spacer arm Enzyme-antibody conjugation | 14.5 A |
| Sulfo-SMPB | Primary amines Sulfhydryls | Extended spacer arm Water-soluble | 14.5 A |
| EDC/Sulfo-NHS | Primary amines Carboxyl groups | Hapten-Carrier conjugation | 0 |
| ABH | Carbohydrates Nonselective | Reacts with sugar groups | 11.9 A |

(MLV) or unilamellar vesicles such as microemulsified liposomes (MEL) and large unilamellar liposomes (LUVET), each containing phosphatidylethanolamine (PE), have linked by established procedures. The inclusion of PE in the liposome provides an active functional residue, a primary amine, on the liposomal surface for cross-linking purposes. ST peptides are bound covalently to discrete sites on the liposome surfaces. The number and surface density of these sites will be dictated by the liposome formulation and the liposome type. The liposomal surfaces may also have sites for non-covalent association. To form covalent conjugates of peptides and liposomes, cross-linking reagents have been studied for effectiveness and biocompatibility. Cross-linking reagents include glutaraldehyde (GAD), bifunctional oxirane (OXR), ethylene glycol diglycidyl ether (EGDE), and a water soluble carbodiimide, preferably 1-ethyl-3-(3-dimethylaminopropyl) carbodiimide (EDC). Through the complex chemistry of cross-linking, linkage of the amine residues of the recognizing substance and liposomes is established.

In another example, heterobifunctional cross-linking reagents and methods of using the cross-linking reagents are described in U.S. Pat. No. 5,889,155, specifically incorporated herein by reference in its entirety. The cross-linking reagents combine a nucleophilic hydrazide residue with an In instances where a particular peptide does not contain a residue amenable for a given cross-linking reagent in its native sequence, conservative genetic or synthetic amino acid changes in the primary sequence can be utilized.

C. Combinations with Traditional Antibiotics

Bacterial cell resistance to antibiotic agents represents a major problem in clinical medicine. One goal of current research is to find ways to improve the overcome antibiotic resistance. In addition, drug combinations are known to reduce the dosages required, and in some cases, produce synergistic effects. Thus, in order to increase the effectiveness of the peptide therapies described herein, it may be desirable to combine these compositions with other agents effective in the treatment of bacterial infections, such as antibiotics. An "antibiotic" agent is capable of negatively affecting bacterial growth in a subject, for example, by killing bacterial cells, reducing the growth rate of bacterial cells, or otherwise increasing the quality of life of the afflicted subject. This process may involve contacting the cells with the peptide the agent(s) at the same time. This may be achieved by contacting the cell with a single composition or pharmacological formulation that includes both the peptide and the antibiotic, or by contacting the cell with two distinct compositions or formulations, at the same time, wherein one composition includes the peptide and the other includes the second agent(s).

Alternatively, the peptide therapy may precede or follow the other agent treatment by intervals ranging from minutes to weeks. In embodiments where the other agent and peptide are applied separately to the cell, one would generally ensure that a significant period of time did not expire between the time of each delivery, such that the agent and peptide would still be able to exert an advantageously combined effect on the cell. In such instances, it is contemplated that one may contact the cell with both modalities within about 12–24 h of each other and, more preferably, within about 6–12 h of each other. In some situations, it may be desirable to extend the time period for treatment significantly, however, where several d (2, 3, 4, 5, 6 or 7) to several wk (1, 2, 3, 4, 5, 6, 7 or 8) lapse between the respective administrations.

Various combinations may be employed, peptide therapy is "A" and the secondary agent is "B":

A/B/A  B/A/B  B/B/A  A/A/B  A/B/B  B/A/A  A/B/B/B  B/A/B/B

B/B/B/A  B/B/A/B  A/A/B/B  A/B/A/B  A/B/B/A  B/B/A/A

B/A/B/A  B/A/A/B  A/A/A/B  B/A/A/A  A/B/A/A  A/A/B/A

Administration of the peptides of the present invention to a patient will follow general protocols for the administration of antibiotics, taking into account the toxicity, if any. It is expected that the treatment cycles would be repeated as necessary. Listed below are some common antibiotics and their respective dosages.

TABLE 2

COMMON ANTIBIOTICS AND USUAL ORAL DOSES

| ANTIBIOTIC | DOSAGE |
|---|---|
| Penicillin V | 250 mg qid |
| Rugby (generic) | |
| V-cillin K | |
| Dicloxacillin | 250 mg qid |
| Glenlawn (generic) | |
| Dynapen | |
| Cloxacillin (Tegopen) | 250 mg qid |
| Amoxicillin | 250 mg tid |
| Rugby (generic) | |
| Polymox | |
| Ampicillin | 250 mg qid |
| Moore (generic) | |
| Polycillin | |
| Augmentin | tid |
| 250-mg tablets | |
| chewables (250 mg) | |
| 125-mg (suspension) | |
| chewables (125 mg) | |
| Carbenicillin (Geocillin) | 382 mg qid (1 tb) 2 tab qid |
| Cephalexin | 250 mg qid |
| Rugby (generic) | |
| Keflex | |
| Rugby (generic) | |
| Keflex | 500 mg qid |
| Cefadroxil | 1 gm bid |
| Rugby (generic) | |
| Duricef | |
| Cephradine | 250 mg qid |
| Rugby (generic | 500 mg qid |
| Velosef | |
| Rugby (generic) | |
| Velosef | |

TABLE 2-continued

COMMON ANTIBIOTICS AND USUAL ORAL DOSES

| ANTIBIOTIC | DOSAGE |
|---|---|
| Cefaclor | 250 mg tid |
| Ceclor | |
| Cefuroxime axetil | 125 mg bid |
| Ceftin | 250 mg bid |
| | 500 mg bid |
| Cefixime | 400 mg q24 h |
| Suprax | |
| Cefprozil | |
| Cefzil | 250 mg q12 h |
| Loracarbef (Lorabid) | 200 mg bid |
| Cefpodoxime proxetil | 200 mg bid |
| (Vantin) | |
| Clindamycin | 300 mg q8 h |
| Cleocin | |
| TMP/SMZ | 1 double-strength bid |

TABLE 2-continued

COMMON ANTIBIOTICS AND USUAL ORAL DOSES

| ANTIBIOTIC | DOSAGE |
|---|---|
| Bactrim | |
| Septra | |
| (generic) | |
| Trimethoprim | 100 mg bid |
| Rugby (generic) | |
| Proloprim | |
| Erythromycin (base) | 250 mg qid |
| Abbott | |
| E-mycin (delayed release) | |
| Erythromycin stearate | 250 mg qid |
| Rugby (generic) | |
| Azithromycin | 1 g once only 500 mg, |
| Zithromax | day 1, plus 250 mg, day 2–5 |
| Clarithromycin | 250 mg bid |
| Biaxin | 500 mg bid |
| Tetracycline hydrochloride | 250 mg qid |
| Mylan | |
| Sumycin 250 | |
| Doxycycline | 100 mg qd (with 200- mg |
| Lederle (generic) | initial load) |
| Vibramycin | |
| Vancomycin | Capsules |
| Vancocin HCl (oral soln/powder) | 125 mg q6 h PO |
| Metronidazole | 250 mg qid |
| Rugby (generic) | |
| Flagyl | |
| Norfloxacin | 400 mg bid |
| Noroxin | |
| Ciprofloxacin | 250 mg bid |
| Cipro | 500 mg bid |
| | 750 mg bid |
| Ofloxacin | 200 mg bid |
| Floxin | 300 mg bid |
| | 400 mg bid |
| Lomefloxacin Maxaquin | 400 mg once qd |

TABLE 3

COMMON ANTIBIOTICS AND USUAL PARENTERAL DOSES

| ANTIBIOTIC | DOSAGE |
|---|---|
| Penicillin G | 2,400,000 units |
| Pfizerpen G (Pfizer) | 12 million units |
| Oxacillin | 12 g |
| Prostaphlin (Bristol) | |
| Nafcillin | 12 g |
| Nafcil (Bristol) | |
| Ampicillin | 6 g |
| Omnipen (Wyeth) | |
| Ticarcillin | 18 g |
| Ticar (Beecham) | |
| Piperacillin | 18 g |
| Pipracil (Lederle) | 16 g |
| Mezlocillin | 18 g |
| Mezlin (Miles) | 16 g |
| Ticarcillin-clavulanate | 18 g/0.6 g |
| Timentin (Beecham) | 12 g/0.4 g |
| Ampicillin-sulbactam | 6 g |
| Unasyn (Roerig) | 12 g |
| Cephalothin | 9 g (1.5 g q4 h) |
| Keflin (Lilly) | |
| Cefazolin | 4 g (1 g q6 h) |
| Ancef (SKF) | 3 g (1 g q8 h) |
| Cefuroxime | 6 g 2.25 g (750 mg q8 h) |
| Zinacef (Glaxo) | 4.5 g (1.5 g q8 h) |
| Cefamandole | 9 g (1.5 g q4 h) |
| Mandol (Lilly) | |
| Cefoxitin | 8 g (2 g q6 h) |
| Mefoxin (MSD) | 6 g (2 g q8 h) |
| Cefonicid | 1 g q12 h |
| Monicid (SKF) | |
| Cefotetan | 2 g q12 h |
| Cefotan (Stuart) | |
| Cefmetazole | 2 g q8 h |
| Zefazone (Upjohn) | |
| Ceftriaxone | 2 g (2.0 g q24 h) |
| Rocephin (Roche) | 1 g (1.0 g q24 h) |
| Ceftazidime | 6 g (2 g q8 h) |
| Fortax (Glaxo) | |
| Taxicef (SKF) | |
| Tozidime (Lilly) | |
| Cefotaxime | 2 g q6 h |
| Claforan (Hoechst) | 2 g q8 h |
| Cefoperazone | 8 g (2 g q6 h) |
| Cefobid (Pfizer) | 6 g (2 g q8 h) |
| Ceftizoxime | (2 g q8 h) |
| Ceftizox (SKF) | |
| Aztreonam | 2 g q8 h |
| Azactam (Squibb) | 1 g q8 h |
| Imipenem | 2000 mg (500 mg 16 h) |
| Primaxin (MSD) | |
| Gentamicin | 360 mg (1.5 mg/kg q8 h |
| Garamycin | for an 80-kg patient) |
| (Schering) | |
| (generic) (Elkins-Sinn) | |
| Tobramycin | 360 mg (1.5 mg/kg q8 h |
| Nebcin (Dista) | for an 80-kg patient) |
| Amikacin | 1200 mg (7.5 mg/kg |
| Amikin (Bristol) | q12 h for an 80-kg patient) |
| Clindamycin | 2400 mg (600 mg q6 h) |
| Cleocin (Upjohn) | 2700 mg (900 mg q8 h) |
| | 1800 mg (600 mg q8 h) |
| Chloramphenicol | 4 g (1 g q6 h) |
| Chloromycetin (P/D) | |
| TMP/SMZ | 1400 mg TMP (5 mg |
| Septra (Burroughs Wellcome) | TMP/kg q6 h for a 70-kg patient) |
| | 700 mg TMP (5 mg TMP/kg q12 h for a 70-kg patient) |
| Erythromycin | 2000 mg (500 mg q6 h) |
| Erythromycin | |
| (Elkins-Sinn) | |
| Doxycycline | 200 mg (100 mg q12 h) |
| Vibramycin (Pfizer) | |

TABLE 3-continued

COMMON ANTIBIOTICS AND USUAL PARENTERAL DOSES

| ANTIBIOTIC | DOSAGE |
|---|---|
| Vancomycin | 2000 mg (500 mg q6 h) |
| Vancocin (Lilly) | |
| Metronidazole | 2000 mg (500 mg q6 h) |
| (generic) (Elkins-Sinn) | |
| Ciprofloxacin | 200 mg q12 h |
| Cipro | 400 mg q12 h |
| Pentamidine | 280 mg (4 mg/kg q24 h |
| Pentam (LyphoMed) | for a 70-kg patient) |

D. Liposomal Delivery

In particular embodiments, the peptides of the present invention may be used in conjunction with lipid delivery vehicles, often called liposomes. A "liposome" is a generic term encompassing a variety of single and multilamellar lipid vehicles formed by the generation of enclosed lipid bilayers or aggregates. Liposomes may be characterized as having vesicular structures with a bilayer membrane, generally comprising a phospholipid, and an inner medium that generally comprises an aqueous composition.

A multilamellar liposome has multiple lipid layers separated by aqueous medium. They form spontaneously when lipids comprising phospholipids are suspended in an excess of aqueous solution. The lipid components undergo self-rearrangement before the formation of closed structures and entrap water and dissolved solutes between the lipid bilayers (Ghosh and Bachhawat, 1991). Lipophilic molecules or molecules with lipophilic regions may also dissolve in or associate with the lipid bilayer.

A liposome used according to the present invention can be made by different methods, as would be known to one of ordinary skill in the art. For example, a phospholipid (Avanti Polar Lipids, Alabaster, Ala.), such as for example the neutral phospholipid dioleoylphosphatidylcholine (DOPC), is dissolved in tert-butanol. The lipid(s) is then mixed with the imexon and/or a derivative thereof, and/or other component(s). Tween 20 is added to the lipid mixture such that Tween 20 is about 5% of the composition's weight. Excess tert-butanol is added to this mixture such that the volume of tert-butanol is at least 95%. The mixture is vortexed, frozen in a dry ice/acetone bath and lyophilized overnight. The lyophilized preparation is stored at −20° C. and can be used up to three months. When required the lyophilized liposomes are reconstituted in 0.9% saline. The average diameter of the particles obtained using Tween 20 is about 0.7 to about 1.0 μm in diameter.

Alternatively, a liposome can be prepared by mixing lipids in a solvent in a container, e.g., a glass, pear-shaped flask. The container should have a volume ten-times greater than the volume of the expected suspension of liposomes. Using a rotary evaporator, the solvent is removed at approximately 40° C. under negative pressure. The solvent normally is removed within about 5 min to 2 hrs, depending on the desired volume of the liposomes. The composition can be dried further in a desiccator under vacuum. The dried lipids generally are discarded after about 1 week because of a tendency to deteriorate with time.

Dried lipids can be hydrated at approximately 25–50 mM phospholipid in sterile, pyrogen-free water by shaking until all the lipid film is resuspended. The aqueous liposomes can be then separated into aliquots, each placed in a vial, lyophilized and sealed under vacuum.

In other alternative methods, liposomes can be prepared in accordance with other known laboratory procedures (e.g., see Bangham et al., 1965; Gregoriadis, 1979; Deamer and Nichols, 1983; Szoka and Papahadjopoulos, 1978, each incorporated herein by reference in relevant part). These methods differ in their respective abilities to entrap aqueous material and their respective aqueous space-to-lipid ratios.

The dried lipids or lyophilized liposomes prepared as described above may be dehydrated and reconstituted in a solution of inhibitory peptide and diluted to an appropriate concentration with an suitable solvent, e.g., DPBS. The mixture is then vigorously shaken in a vortex mixer. Unencapsulated additional materials, such as agents including but not limited to hormones, drugs, nucleic acid constructs and the like, are removed by centrifugation at 29,000×g and the liposomal pellets washed. The washed liposomes are resuspended at an appropriate total phospholipid concentration, e.g., about 50–200 mM. The amount of additional material or active agent encapsulated can be determined in accordance with standard methods. After determination of the amount of additional material or active agent encapsulated in the liposome preparation, the liposomes may be diluted to appropriate concentrations and stored at 4° C. until use. A pharmaceutical composition comprising the liposomes will usually include a sterile, pharmaceutically acceptable carrier or diluent, such as water or saline solution.

The size of a liposome varies depending on the method of synthesis. Liposomes in the present invention can be a variety of sizes. In certain embodiments, the liposomes are small, e.g., less than about 100 nm, about 90 nm, about 80 nm, about 70 nm, about 60 nm, or less than about 50 nm in external diameter. In preparing such liposomes, any protocol described herein, or as would be known to one of ordinary skill in the art may be used. Additional non-limiting examples of preparing liposomes are described in U.S. Pat. Nos. 4,728,578, 4,728,575, 4,737,323, 4,533,254, 4,162,282, 4,310,505, and 4,921,706; International Applications PCT/US85/01161 and PCT/US89/05040; U.K. Patent Application GB 2193095 A; Mayer et al., 1986; Mayhew et al., 1984, each incorporated herein by reference).

A liposome suspended in an aqueous solution is generally in the shape of a spherical vesicle, having one or more concentric layers of lipid bilayer molecules. Each layer consists of a parallel array of molecules represented by the formula XY, wherein X is a hydrophilic moiety and Y is a hydrophobic moiety. In aqueous suspension, the concentric layers are arranged such that the hydrophilic moieties tend to remain in contact with an aqueous phase and the hydrophobic regions tend to self-associate. For example, when aqueous phases are present both within and without the liposome, the lipid molecules may form a bilayer, known as a lamella, of the arrangement XY-YX. Aggregates of lipids may form when the hydrophilic and hydrophobic parts of more than one lipid molecule become associated with each other. The size and shape of these aggregates will depend upon many different variables, such as the nature of the solvent and the presence of other compounds in the solution.

The production of lipid formulations often is accomplished by sonication or serial extrusion of liposomal mixtures after (I) reverse phase evaporation (II) dehydration-rehydration (III) detergent dialysis and (IV) thin film hydration. In one aspect, a contemplated method for preparing liposomes in certain embodiments is heating sonicating, and sequential extrusion of the lipids through filters or membranes of decreasing pore size, thereby resulting in the formation of small, stable liposome structures. This preparation produces liposomes only of appropriate and uniform size, which are structurally stable and produce maximal activity. Such techniques are well-known to those of skill in the art (see, for example Martin, 1990).

Numerous disease treatments are using lipid based gene transfer strategies to enhance conventional or establish novel therapies. Advances in liposome formulations have improved the efficiency of gene transfer in vivo (Templeton et al., 1997) and it is contemplated that liposomes are prepared by these methods. Alternate methods of preparing lipid-based formulations for nucleic acid delivery are described (WO 99/18933).

In another liposome formulation, an amphipathic vehicle called a solvent dilution microcarrier (SDMC) enables integration of particular molecules into the bilayer of the lipid vehicle (U.S. Pat. No. 5,879,703). The SDMCs can be used to deliver lipopolysaccharides, polypeptides, nucleic acids and the like. Of course, any other methods of liposome preparation can be used by the skilled artisan to obtain a desired liposome formulation in the present invention.

E. Therapeutic Uses

1. Formulations and Routes of Administration

Pharmaceutical aqueous compositions of the present invention comprise an effective amount of a peptide dissolved or dispersed in a pharmaceutically acceptable carrier or aqueous medium. The phrases "pharmaceutically or pharmacologically acceptable" refer to molecular entities and compositions that do not produce an adverse, allergic or other untoward reaction when administered to a human. As used herein, "pharmaceutically acceptable carrier" includes any and all solvents, dispersion media, antibacterial and antifungal agents, isotonic and absorption delaying agents and the like. The use of such media and agents for pharmaceutical active substances is well known in the art. Except insofar as any conventional media or agent is incompatible with the active ingredient, its use in the therapeutic compositions is contemplated. Supplementary active ingredients can also be incorporated into the compositions. The compositions will be sterile, be fluid to the extent that easy syringability exists, stable under the conditions of manufacture and storage.

The actual dosage amount of a composition of the present invention administered to a patient can be determined by physical and physiological factors such as body weight, severity of condition, idiopathy of the patient and on the route of administration. With these considerations in mind, the dosage of a lipid composition for a particular subject and/or course of treatment can readily be determined.

Although it is most preferred that compositions of the present invention be prepared in sterile water containing other non-active ingredients, made suitable for injection, solutions of such active ingredients can also be prepared in water suitably mixed with a surfactant, such as hydroxypropylcellulose, if desired. Dispersions can also be prepared in liquid polyethylene glycols, and mixtures thereof and in oils. The carrier can also be a solvent or dispersion medium containing, for example, water, ethanol, polyol (for example, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion and by the use of surfactants.

The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Upon formulation, solutions will be administered in a manner compatible with the dosage formulation and in such amount as is therapeutically effective. For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, sterile aqueous media which can be employed will be known to those of skill in the art in light of the present disclosure. Some variation in dosage will necessarily occur depending on the condition of the subject being treated. The person responsible for administration will, in any event, determine the appropriate dose for the individual subject.

2. Indications

The present invention provides for methods of preventing and treating bacterial infections. In particular, the methods are designed to inhibit *H. influenzae* and *S. aureus*. As discussed above, *Haemophilus influenzae* type b (Hib) used to be the most frequent cause of neonatal meningitis and other invasive infections of infants and young children in the United States (Fraser et al., 1974). And even though effective vaccines now exist, some are of limited utility in the case of young children, the group most at risk for severe Hib infections. In addition, current vaccines are is not effective against disease caused by non-typeable *Haemophilus influenzae* (NTHi), which can cause pneumonia, bacteremia, meningitis, postpartum sepsis, and otitis media in children and young adults.

Similarly, *S. aureus* causes skin lesions such as boils, styes and furuncles, more serious infections such as pneumonia, mastitis, phlebitis, meningitis, eyelid infections, neonatal conjunctivitis, urinary tract infections, and deep-seated infections, such as joint infections, osteomyelitis and endocarditis. It also is a major cause of nosocomial infections, particularly those involving surgical wounds and burns, and causes food poisoning by releasing enterotoxins into food, and toxic shock syndrome by release of pyrogenic exotoxins into the blood stream. Thus, the present invention contemplates the treatment and/or prevention of each of the foregoing conditions.

The compositions of the present invention can be administered intravenously, intradermally, intraarterially, intraperitoneally, intralesionally, intracranially, intraarticularly, intraprostaticaly, intrapleurally, intratracheally, intranasally, intravitreally, intravaginally, rectally, topically, intramuscularly, intraperitoneally, subcutaneously, intravesicularlly, mucosally, intrapericardially, orally, topically, locally using aerosol, injection, infusion, continuous infusion, localized perfusion bathing target cells directly or via a catheter or lavage. Typically, such compositions are prepared as injectables, either as liquid solutions or suspensions; solid forms suitable for preparing solutions or suspensions upon the addition of a liquid prior to injection can also be prepared; and the preparations can also be emulsified.

3. Medical Devices

The invention also provides medical devices coated with a composition comprising an antimicrobial peptide. Examples of medical devices include endotracheal tubes, a vascular catheter, an urinary catheter, a nephrostomy tube, a biliary stent, a peritoneal catheter, an epidural catheter, a central nervous system catheter, an orthopedic device, a prosthetic valve, and a medical implant. The vascular catheter may be a central venous catheter, an arterial line, an pulmonary artery catheter, and a peripheral venous catheter. The central nervous system catheter may be an intraventricular shunt. Other medical devices that can benefit from the present invention include blood exchanging devices, vascular access ports, cardiovascular catheters, extracorpeal circuits, stents, implantable prostheses, vascular grafts, pumps, heart valves, and cardiovascular sutures, to name a few. Regardless of detailed embodiments, applicability of the invention should not be considered limited with respect to the type of medical device, implant location or materials of construction of the device.

F. Kits

Any of the compositions described herein may be comprised in a kit. In a non-limiting example, a peptide or analogue thereof may be comprised in a kit. The kits will thus comprise, in suitable container means, a peptide, with optional additional agents of the present invention, such as linking reagents or antibiotic agents.

The kits may comprise a suitably aliquoted peptide or analogues thereof, whether conjugated or not. The components of the kits may be packaged either in aqueous media or in lyophilized form. The container means of the kits will generally include at least one vial, test tube, flask, bottle, syringe or other container means, into which a component may be placed, and preferably, suitably aliquoted. Where there is more than one component in the kit, the kit also will generally contain a second, third or other additional container into which the additional components may be separately placed. However, various combinations of components may be comprised in a vial. The kits of the present invention also will typically include a means for containing the containers in close confinement for commercial sale. Such means may include injection or blow-molded plastic containers into which the desired vials are retained.

G. EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

1. Materials and Methods

Int-1, a non-typeable clinical isolate, was isolated in 1991 from the blood of a child with clinical symptoms of meningitis. It is virulent in rat models and is able to survive in human serum. Kw20, a non-typeable strain, was isolated in 1954. R3001, a non-typeable clinical isolate, was isolated from a bronchial lavage of a cystic fibrosis patient. R2140, is a non-typeable clinical isolate. R538 is a *Haemophilus influenzae* type b ATCC strain No. 9795. E1a is a type b *Haemophilus influenzae* clinical isolate.

Using a while cell affinity selection procedure, the fUSE5-15 and f88/4-15mer phage-displayed libraries were pre-adsorbed twice against the non-pathogenic strain ($Kw^{20}$), prior to three affinity selections against the virulent strain, Int-1 (FIG. 1).

2. Results

Figure 2:
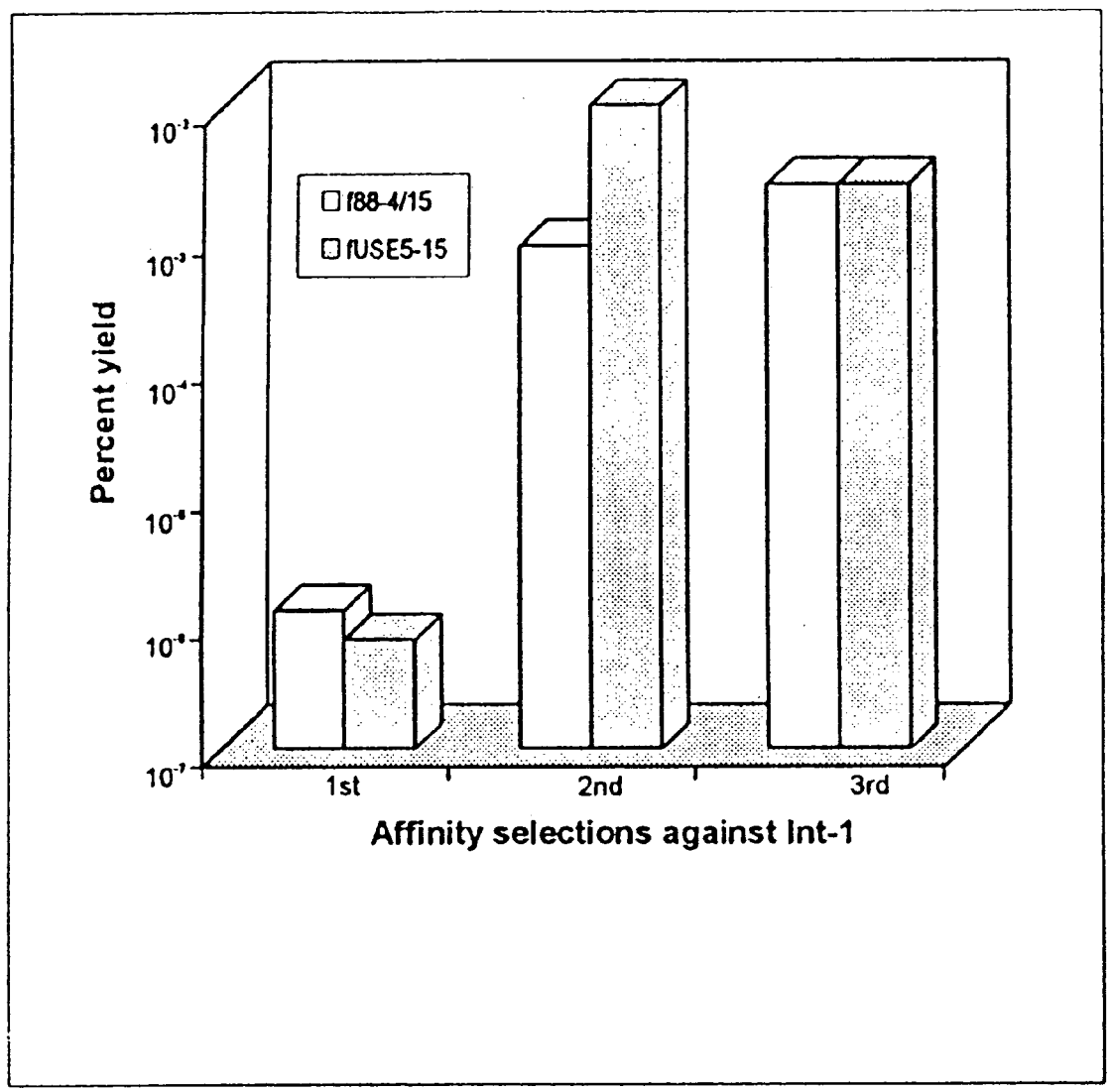
FIG. 2—Selection for Int-1 binding phage—the percent yields during affinity selections. Input titers were between $10^{11}$ and $10^{12}$ TU for each round of affinity selection. Phage binding to Int-1 were eluted and titered by *E. coli* infection and expressed as percent yield.

There was over 2000-fold enrichment for Int-1 binding phage over three rounds of affinity selection against Int-1. The majority of this enrichment occurred between the first and second rounds of affinity selection (700-fold; FIG. 2).

Pre-adsorbing the phage-displayed libraries against $Kw^{20}$ effectively subtracted out the highly expressed epitopes common to both Int-1 and $Kw^{20}$. This resulted in a set of peptides that bound to both Int-1 and $Kw^{20}$ to low levels.

Table 4 shows the bactericidal phage-displayed peptides divided into three groups based on their bactericidal activities towards Int-1: Group 1—hi3/17; Group 2—hi3/2, hi3/12, hi3/11; Group 3—hi3/13 and fUSE5/2. hi3/17 showed over 5-fold greater antimicrobial activity towards Int-1 (MIC~1e10 virions per μl) compared with Group 2 phage displayed peptides.

70% to 90% of Int-1 binding to plastic, whereas the vector control showed less than 20% inhibition.

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the compositions and methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

TABLE 4

Summary of antimicrobial peptides from f88-4/15mer and fUSE5-15mer libraries

| Library | Group | Clone | Frequency[1] | Amino Acid Sequence | pI | MIC | IC90 |
|---|---|---|---|---|---|---|---|
| fUSE5-15/mer | 1 | fuse5/2 | 1/12 | VVFLSSRNSAVFTDF | 5.81 | 1.99e10 | 1.86e10 |
| f88-4/15-mer | 2 | hi3/2 | 1/15 | GRHRTSVPTDEVFIT | 6.75 | 9.98e9 | 9.19e9 |
| | | hi3/12 | 1/15 | KKSHHPSSEWGLNLT | 8.61 | 9.98e9 | 8.92e9 |
| | | hi3/11 | 1/15 | KQRDSRSGYTAPTLV | 9.99 | 9.98e9 | 8.92e9 |
| | | hi3/13 | 1/15 | RNHGTDRATTIPPLS | 9.61 | 2.29e10 | 1.93e10 |
| | 3 | hi3/17 | 4/15 | KQRTSIRATEGCLPS | 9.50 | 1.93e9 | 1.82e9 |

[1]frequency of the clone in the library

TABLE 5

Other peptides

| Library | Clone | Freq. In Library | Amino acid sequence |
|---|---|---|---|
| FUSE5-15mer | fUSE5/3 | 1/12 | GSRGKHTFVRPTLVF |
| | fUSE5/8 | 1/12 | FISYSSPSHMGARMR |

Figure 3A:
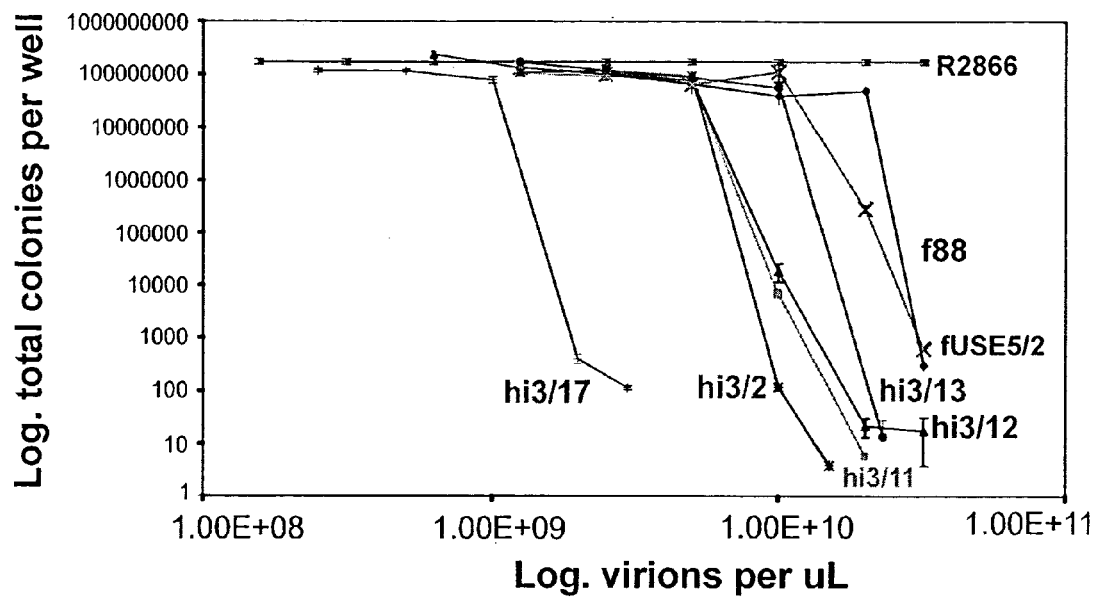
FIGS. 3A & 3B—Inhibition of Int-1 growth using hi3/17, hi3/2, hi3/11, hi3/12, hi3/13 and fUSE5/2 phage-displayed peptides. Int-1 (150 µl) was incubated overnight in the presence of the two-fold dilutions of phage-displayed peptides in sBHI broth (supplemented with 10 µg/mL heme and NAD+) at 37° C. The next day, the optical densities of the bacterial cultures were evaluated by direct measurement of the optical densities at $OD_{630}$ nm. Dilutions of the bacteria were incubated on sBHI agar plates to determine the total number of colonies per well (FIG. 3A) and this data was also expressed as percent inhibition of growth (FIG. 3B).
Figure 3B:
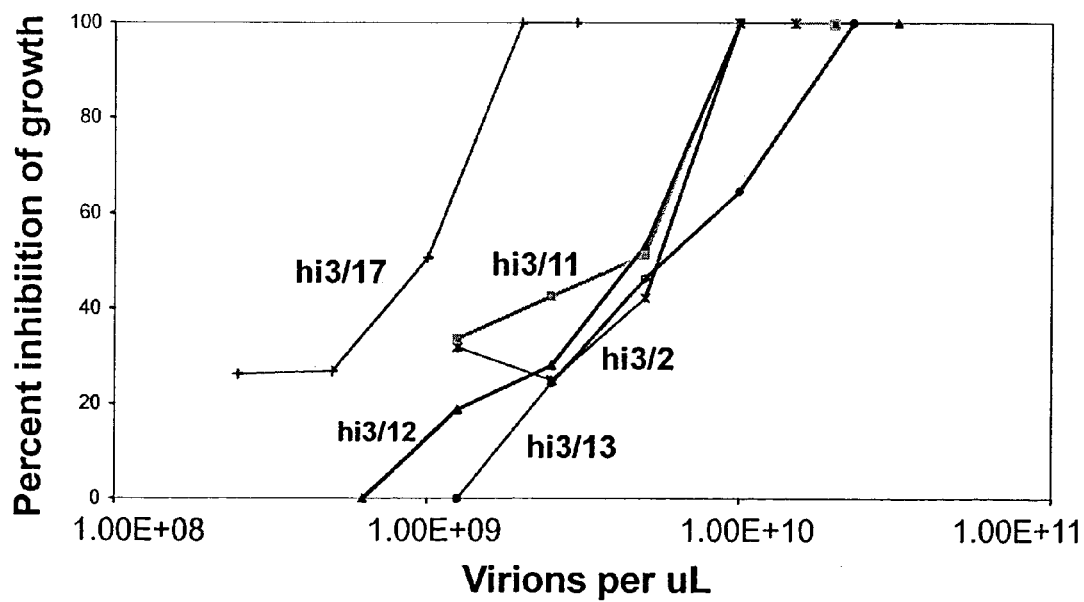

The fUSE5/2 and hi3/17 phage-displayed peptides were bactericidal against Int-1. The concentration required to inhibit 90% of bacterial growth (IC$_{90}$) was $1.77 \times 10^{10}$ virions for fUSE5/2 and $2.39 \times 10^9$ virions for hi3/17 (FIGS. 3A and 3B). Microscopic results indicated that these peptides altered the cell membrane integrity of NTHi. The MIC concentration resulting in no bacterial growth was $2.4 \times 10^{10}$ virions for fUSE5/2 and $3.64 \times 10^9$ virions for hi3/17 (FIGS. 3A and 3B).

Figure 4:
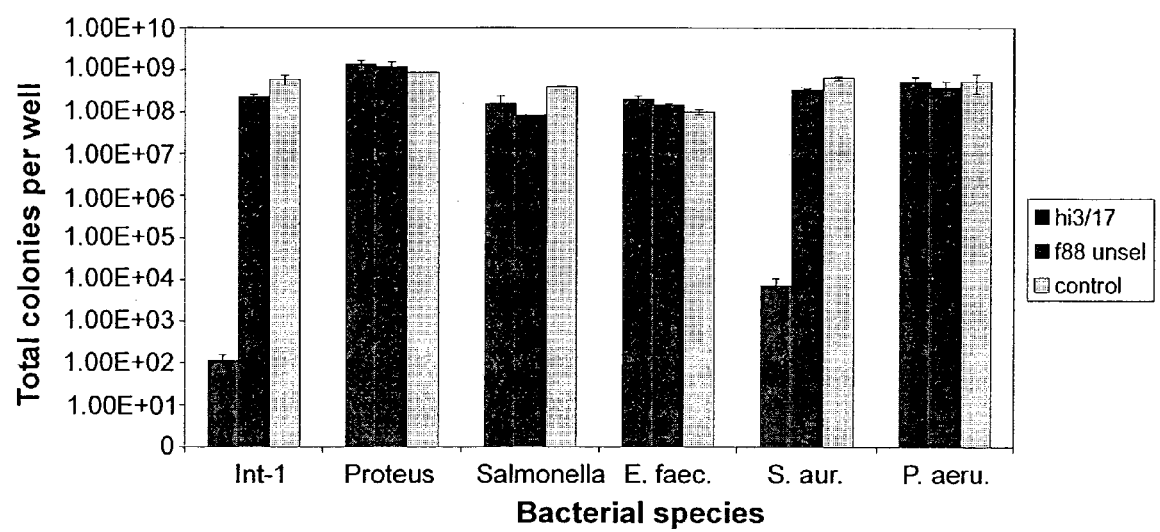
FIG. 4—Effect of phage displayed peptide hi3/17 on growth of *Haemophilus influenzae* (Int-1), *Proteus mirabilis* (*Proteus*), *salmonella* spp. (*Salmonella*), *Enterococcus faecialis* (*E. faec.*), *Staphylococcus aureus* (*S. aur.*) and *Pseudomonas aeruginosa* (*P. aeru.*). One hundred and fifty µl of the test bacteria were incubated in the presence of either hi3/17, f88 unselected phage display library in sBHI broth (supplemented with 10 µg/mL heme and NAD+) or control sBHI at 37° C. The next day, the optical densities of the bacterial cultures were evaluated by direct measurement of the optical densities at $OD_{630}$ nm. Dilutions of the bacteria were incubated on sBHI agar plates to determine the total number of colonies per well.
Figure 5:
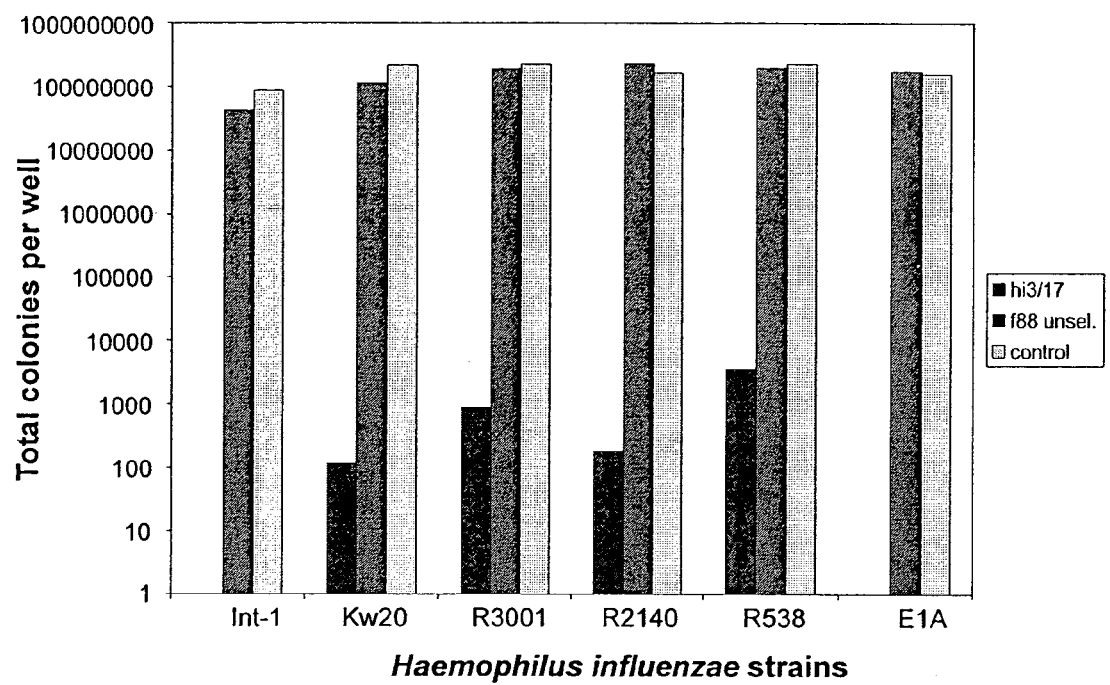
FIG. 5—Effect of hi3/17 phage displayed peptide on growth of *Haemophilus influenzae* strains Int-1, Kw20, R3001, R2140, R538 and E1A. One hundred and fifty µl of the test bacteria were incubated in the presence of either hi3/17, f88 unselected phage display library in sBHI broth (supplemented with 10 µg/mL heme and NAD+) or control sBHI broth at 37° C. The next day, the optical densities of the bacterial cultures were evaluated by direct measurement of the optical densities at $OD_{630}$ nm. Dilutions of the bacteria were incubated on sBHI agar plates to determine the total number of colonies per well.
Figure 6:
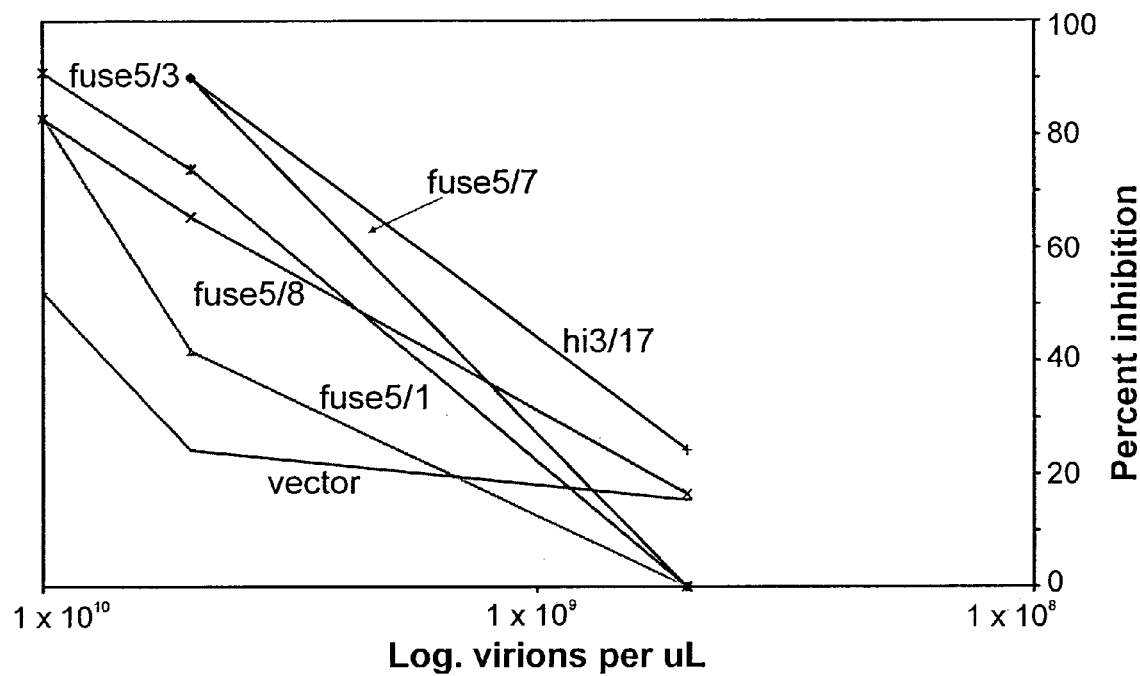
FIG. 6—Effect of hi3/17 on adhesion of Int-1 to plastic. Two-fold dilutions of phage-displayed peptides were incubated with $1 \times 10^5$ transducing units (1 transducing unit=1 colony after overnight incubation) for 1 hour at 37° C. in a 96-well microtiter plate. The plates were then washed to remove unbound bacteria. Binding of Int-1 was detected spectrophotometrically at 410 nm using the p-nitrophenyl phosphate reaction. The amount of Int-1 binding to plastic was calculated from a standard curve prepared from known amounts of Int-1.

The fUSE5/2 and hi3/17 phage-displayed peptides showed a similar level of antimicrobial activity towards other *H. influenzae* strains tested, including the encapsulated type b strain (Hib) (data not shown). When tested for antimicrobial activity against other bacterial species, hi3/17 was able to completely inhibit the growth of *Staphylococcus aureus* and showed no activity against *Proteus* or *Enterococcus faecialis*, despite binding being detectable via ELISA (FIG. 4).

The phage-displayed peptides were able to inhibit binding of NTHi to plastic. At a phage concentration of $1 \times 10^9$ virions, fUSE5/3, fUSE5/7 and hi3/17 inhibited between H. References The following references, to the extent that they provide exemplary procedural or other details supplementary to those set forth herein, are specifically incorporated herein by reference.

U.S. Pat. No. 4,162,282
U.S. Pat. No. 4,310,505
U.S. Pat. No. 4,533,254
U.S. Pat. No. 4,728,575
U.S. Pat. No. 4,728,578
U.S. Pat. No. 4,737,323
U.S. Pat. No. 4,921,706
U.S. Pat. No. 5,401,511
U.S. Pat. No. 5,603,872
U.S. Pat. No. 5,879,703
U.S. Pat. No. 5,889,155
U.S. Pat. No. 6,020,154
U.K. Appln. GB 2193095A
Intl Appln. PCT/US85/01161
Intl Appln. PCT/US89/05040
Intl Appln. WO 99/18933
Bangham, Standish, Watkins, "Diffusion of univalent ions across the lamellae of swollen phospholipids," *J. Mol. Biol.*, 13(1):238–52, 1965.
Bergey's Manual, 1992.
Bodanszky, Henes, Natarajan, Stahl, "High resolution mass spectra of malformin and related cyclic peptides," *J. Antibiot.*, (Tokyo), 29(5):549–553, 1986.

Boyle-Vavra, Berke, Lee, Daum, "Reversion of the glycopeptide resistance phenotype in *Staphylococcus aureus* clinical isolates," *Antimicrob. Agents Chemother.*, 44(2): 272–277, 2000.

Deamer and Nichols, "Proton-hydroxide permeability of liposomes," *Proc. Natl. Acad. Sci. USA*, 80(1):165–168, 1983.

Fraser, Geil, Feldman, "Bacterial meningitis in Bernalillo County, New Mexico: a comparison with three other American populations," *Am. J. Epidemiol.*, 100(1):29–34, 1974.

Ghosh and Bachhawat, Targeting of Liposomes to Hepatocytes. In: *Liver Diseases, Targeted Diagnosis and Therapy Using Specific Receptors and Ligands*. Wu et al., eds., Marcel Dekker, New York, pp. 87–104, 1991.

Granoff, Shackelford, Pandey, Boies, "Antibody responses to *Haemophilus influenzae* type b polysaccharide vaccine in relation to Km(1) and G2m(23) immunoglobulin allotypes," *J. Infect. Dis.*, 154(2):257–264, 1986.

Gregoriadis and Davis, "Stability of liposomes in vivo and in vitro is promoted by their cholesterol content and the presence of blood cells," *Biochem. Biophys. Res. Commun.*, 89(4):1287–1293, 1979.

Hanson and Hanse, "Molecular cloning, partial purification, and characterization of a haemin-binding lipoprotein from *Haemophilus influenzae* type b," *Mol. Microbiol.*, 5(2): 267–278, 1991.

Hanson, Pelzel, Latimer, Muller-Eberhard, Hansen, "Identification of a genetic locus of *Haemophilus influenzae* type b necessary for the binding and utilization of heme bound to human hemopexin," *Proc. Natl. Acad. Sci. USA*, 89(5):1973–1977, 1992.

Lee, "Isolation of an outer membrane hemin-binding protein of *Haemophilus influenzae* type b," *Infect. Immun.*, 60(3): 810–816, 1992.

Martin, "High efficiency Ca2+ transport by the sarcoplasmic reticulum Ca2(+)-ATPase in the absence of the 53-kilodalton glycoprotein," *J. Biol. Chem.*, 265(34):20946–20951, 1990.

Mayer, Hope, Cullis, "Vesicles of variable sizes produced by a rapid extrusion procedure," *Biochim. Biophys. Acta*, 858(1):161–168, 1986.

Mayhew, Lazo, Vail, King, Green, "Characterization of liposomes prepared using a microemulsifier," *Biochim. Biophys. Acta*, 775(2):169–174, 1984.

Murphy and Apicella, "Antigenic heterogeneity of outer membrane proteins of nontypable *Haemophilus influenzae* is a basis for a serotyping system," *Infect. Immun.*, 50(1):15–21, 1985.

Peptide Synthesis, John Wiley and Sons, 2d Ed.; Kent and Clark-Lewis In: *Synthetic Peptides in Biology and Medicine*, Alitalo et al. (Eds.), 295–358, Science Publishers, Amsterdam, 1985.

Ploy, Grelaud, Martin, de Lumley, Denis, "First clinical isolate of vancomycin-intermediate *Staphylococcus aureus* in a French hospital," *Lancet*, 351(9110):1212, 1998.

Shenep, Munson, Jr, Barenkamp, Granoff, "Further studies of the role of noncapsular antibody in protection against experimental *Haemophilus influenzae* type b bacteremia," *Infect. Immun.*, 42(1):257–263, 1983.

Stewart and Young, Solid Phase Peptide Synthesis, 2d. ed., Pierce Chemical Co., 1984.

Szoka and Papahadjopoulos, "Procedure for preparation of liposomes with large internal aqueous space and high capture by reverse-phase evaporation," *Proc. Natl. Acad. Sci. USA*, 75(9):4194–4198, 1978.

Templeton, Lasic, Frederik, Strey, Roberts, Pavlakis, "Improved DNA: liposome complexes for increased systemic delivery and gene expression," *Nat. Biotechnol.* 15(7):647–652, 1997.

Tiller and Buckley, "Transient hypogammaglobulinemia of infancy: review of the literature, clinical and immunologic features of 11 new cases, and long-term follow-up," *J. Pediatr.*, 92(3):347–353, 1978.

Udo, Wei, Grubb, "Conjugative trimethoprim resistance in *Staphylococcus aureus*," *FEMS Microbiol. Lett.*, 76(3): 243–248, 1992.

Wong, Ho, Woo, Yuen, "Bacteremia caused by *staphylococci* with inducible vancomycin heteroresistance," *Clin. Infect. Dis.*, 29(4):760–767, 1999.

What is claimed is:

1. A method for inhibiting the growth of a *Staphylococcal* or *Haemophilus* species comprising contacting said species with a peptide comprising the sequence.

2. The method of claim 1, wherein said species is a *Staphylococcal* species.

3. The method of claim 2, wherein said *Staphylococcal* species is *S. aureus*.

4. The method of claim 1, wherein said species a *Haemophilus* species.

5. The method of claim 4, wherein said *Haemophilus* species is *H. influenzae*.

6. The method of claim 5, wherein said *H. influenzae* species is non-typeable *H. influenzae*.

7. The method of claim 1, wherein said peptide is between 15 and about 50 residues in length.

8. The method of claim 1, wherein said peptide is between 15 and about 25 residues in length.

9. The method of claim 1, wherein said peptide is 15 residues in length.

10. The method of claim 1, further comprising contacting said species with a chemopharmaceutical antibiotic.

11. A method for treating a *Staphylococcal* or *Haemophilus* species bacterial infection in a subject comprising contacting said subject with a peptide comprising the sequence KQRTSIRATEGCLPS (SEQ ID NO:4) in an amount sufficient to inhibit the growth of bacteria in vivo.

12. The method of claim 11, wherein said *Staphylococcal* species is *S. aureus*.

13. The method of claim 11, wherein said *Haemophilus* species is *H. influenzae*.

14. The method of claim 13, wherein said *H. influenzae* species is non-typeable *H. influenzae*.

15. The method of claim 11, wherein said peptide is between 15 and about 50 residues in length.

16. The method of claim 11, wherein said peptide is between 15 and 25 residues in length.

17. The method of claim 11, wherein said peptide is 15 residues in length.

18. The method of claim 11, wherein said peptide is delivered locally or regionally to a site of infection.

19. The method of claim 18, wherein said peptide is administered to a wound site.

20. The method of claim 18, wherein said peptide is administered topically.

21. The method of claim 11, wherein said peptide is delivered systemically.

22. The method of claim 21, wherein said peptide is delivered via intravenous or intraarterial injection.

23. The method of claim 11, further comprising administering to said subject a chemopharmaceutical antibiotic.

24. A method for preventing a *Staphylococcal* or *Haemophilus* bacterial infection in a subject comprising contacting said subject with a peptide comprising the sequence KQRTSIRATEGCLPS (SEQ ID NO:4) in an amount sufficient to inhibit the growth of bacteria in vivo.

25. A method for preventing *Staphylococcal* or *Haemophilus* bacterial growth in a solution comprising mixing said solution with a peptide comprising the sequence KQRTSIRATEGCLPS (SEQ ID NO:4) in an amount sufficient to inhibit the growth of bacteria in said solution.

26. A method for preventing *Staphylococcal* or *Haemophilus* bacterial attachment or growth on an abiotic surface comprising coating said surface with a peptide comprising the sequence KQRTSIRATEGCLPS (SEQ ID NO:4) in an amount sufficient to inhibit the growth of bacteria on said abiotic surface.

27. The method of claim 26, wherein said surface is part of a medical device.

28. The method of claim 27, wherein said medical device is a syringe, a stent, a catheter, fluid container, a pacemaker, or an implantable pump.

29. A medical device, a surface of which is coated with a peptide comprising the sequence KQRTSIRATEGCLPS (SEQ ID NO:4) in an amount sufficient to inhibit the growth of *Stayhylococcal* or *Haemophilus* bacteria in vivo.

30. The device of claim 29, wherein said medical device is a syringe, a stent, a catheter, fluid container, a pacemaker, a bandage, or an implantable pump.

31. The device of claim 29, wherein said medical device is coated with a second antibiotic agent.

32. An isolated peptide of 15 to about 50 residues comprising the sequence KQRTSIRATEGCLPS (SEQ ID NO:4).

33. A method for identifying a *Staphylococcal* or *Haemophilus* bacterial receptor comprising:
    (a) providing a sample suspected of comprising a bacterial receptor;
    (b) providing a peptide comprising the sequence KQRTSIRATEGCLPS (SEQ ID NO:4);
    (c) contacting said sample with said peptide; and
    (d) identifying a receptor that binds to said peptide.

34. The method of claim 33, wherein said sample is a whole bacterium.

35. The method of claim 33, wherein said sample is a bacterial cell wall.

36. The method of claim 33, wherein said peptide is fixed to a support.

37. The method of claim 36, wherein said support is a filter, a column, a bead, a dipstick or a gel.

38. The method of claim 33, further comprising degradative sequencing of said identified receptor.

39. The method of claim 38, further comprising designing a degenerative probe based on the sequence of said identified receptor.

40. The method of claim 39, further comprising using said degenerative probe to identify the gene encoding said identified receptor.

* * * * *

UNITED STATES PATENT AND TRADEMARK OFFICE
CERTIFICATE OF CORRECTION

PATENT NO. : 7,238,669 B2 Page 1 of 1
APPLICATION NO. : 10/655562
DATED : July 3, 2007
INVENTOR(S) : Bishop-Hurley et al.

It is certified that error appears in the above-identified patent and that said Letters Patent is hereby corrected as shown below:

In claim 29, column 28, line 31, delete "Stayhylococcal" and insert -- Staphylococcal-- therefor.

Signed and Sealed this

Thirtieth Day of October, 2007

JON W. DUDAS
*Director of the United States Patent and Trademark Office*

SEQUENCE LISTING

```
<160> NUMBER OF SEQ ID NOS: 8

<210> SEQ ID NO 1
<211> LENGTH: 5
<212> TYPE: PRT
<213> ORGANISM: Artificial Sequence
<220> FEATURE:
<223> OTHER INFORMATION: Description of Artificial Sequence:  Synthetic
      Peptide

<400> SEQUENCE: 1

Ile Thr Phe Thr Gly
 1               5

<210> SEQ ID NO 2
<211> LENGTH: 19
<212> TYPE: PRT
<213> ORGANISM: Artificial Sequence
<220> FEATURE:
<223> OTHER INFORMATION: Description of Artificial Sequence:  Synthetic
```

Peptide

<400> SEQUENCE: 2

Ala Cys Gly Gly Ala Cys Ala Gly Ala Thr Gly Cys Ala Gly Ala Thr
1               5                   10                  15

Thr Gly Gly

<210> SEQ ID NO 3
<211> LENGTH: 22
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 3

Cys Cys Gly Ala Gly Gly Cys Cys Ala Gly Thr Thr Gly Ala Gly Ala
1               5                   10                  15

Thr Cys Ala Gly Thr Cys
            20

<210> SEQ ID NO 4
<211> LENGTH: 333
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 4

Ala Glu Thr His Val Thr Gly Gly Ser Ala Gly His Thr Val Ser Gly
1               5                   10                  15

Phe Val Ser Leu Leu Ala Pro Gly Ala Lys Gln Asn Val Gln Leu Ile
            20                  25                  30

Asn Thr Asn Gly Ser Trp His Leu Asn Ser Thr Ala Leu Asn Cys Asn
        35                  40                  45

Asp Ser Leu Asn Thr Gly Trp Leu Ala Gly Leu Phe Tyr His His Lys
    50                  55                  60

Phe Asn Ser Ser Gly Cys Pro Glu Arg Leu Ala Ser Cys Arg Pro Leu
65                  70                  75                  80

Thr Asp Phe Asp Gln Gly Trp Gly Pro Ile Ser Tyr Ala Asn Gly Ser
                85                  90                  95

Gly Pro Asp Gln Arg Pro Tyr Cys Trp His Tyr Pro Lys Pro Cys
                100                 105                 110

Gly Ile Val Pro Ala Lys Ser Val Cys Gly Pro Val Tyr Cys Phe Thr
            115                 120                 125

Pro Ser Pro Val Val Gly Thr Thr Asp Arg Ser Gly Ala Pro Thr
    130                 135                 140

Tyr Ser Trp Gly Glu Asn Asp Thr Asp Val Phe Val Leu Asn Asn Thr
145                 150                 155                 160

Arg Pro Pro Leu Gly Asn Trp Phe Gly Cys Thr Trp Met Asn Ser Thr
                165                 170                 175

Gly Phe Thr Lys Val Cys Gly Ala Pro Pro Cys Val Ile Gly Gly Ala
            180                 185                 190

Gly Asn Asn Thr Leu His Cys Pro Thr Asp Cys Phe Arg Lys His Pro
        195                 200                 205

Asp Ala Thr Tyr Ser Arg Cys Gly Ser Gly Pro Trp Ile Thr Pro Arg
    210                 215                 220

```
Cys Leu Val Asp Tyr Pro Tyr Arg Leu Trp His Tyr Pro Cys Thr Ile
225                 230                 235                 240

Asn Tyr Thr Ile Phe Lys Ile Arg Met Tyr Val Gly Gly Val Glu His
            245                 250                 255

Arg Leu Glu Ala Ala Cys Asn Trp Thr Arg Gly Glu Arg Cys Asp Leu
        260                 265                 270

Glu Asp Arg Asp Arg Ser Glu Leu Ser Pro Leu Leu Leu Thr Thr Thr
    275                 280                 285

Gln Trp Gln Val Leu Pro Cys Ser Phe Thr Thr Leu Pro Ala Leu Ser
290                 295                 300

Thr Gly Leu Ile His Leu His Gln Asn Ile Val Asp Val Gln Tyr Leu
305                 310                 315                 320

Tyr Gly Val Gly Ser Ser Ile Ala Ser Trp Ala Ile Lys
                325                 330

<210> SEQ ID NO 5
<211> LENGTH: 24
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 5

Ala Ser Pro Thr Tyr Arg Leu Tyr Ser Ala Ser Pro Ala Ser Pro Ala
1               5                   10                  15

Ser Pro Ala Ser Pro Leu Tyr Ser
            20

<210> SEQ ID NO 6
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 6

Gly Ser Arg Gly Lys His Thr Phe Val Arg Pro Thr Leu Val Phe
1               5                   10                  15

<210> SEQ ID NO 7
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 7

Phe Ile Ser Tyr Ser Ser Pro Ser His Met Gly Ala Arg Met Arg
1               5                   10                  15

<210> SEQ ID NO 8
<211> LENGTH: 43
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 8

Ala Ala Thr Thr Thr Ala Ala Thr Ala Cys Gly Ala Cys Thr Cys Ala
1               5                   10                  15
```

-continued

```
Cys Thr Ala Thr Ala Gly Gly Cys Ala Ala Ala Cys Gly Ala Cys Thr
                20                  25                  30
Gly Thr Cys Cys Thr Gly Gly Cys Cys Gly Thr
            35                  40
```